US006911207B1

(12) United States Patent
Jochmus et al.

(10) Patent No.: US 6,911,207 B1
(45) Date of Patent: Jun. 28, 2005

(54) CYTOTOXIC T-CELL EPITOPES OF THE PAPILLOMAVIRUS L1-PROTEIN AND USE THEREOF IN DIAGNOSTICS AND THERAPY

(75) Inventors: Ingrid Jochmus, Gröbenzell (DE); John Nieland, Stockdorf (DE); Wolfram Osen, Heidelberg (DE); Stefan Faath, Gröbenzell (DE); Klaus Schäfer, Lampertheim (DE)

(73) Assignees: MediGene Aktiengesellschaft, Planegg/Martinsried (DE); Deutsches Krebsfolschungszentrum, Heidelberg (DE)

( * ) Notice: Subject to any disclaimer, the term of this patent is extended or adjusted under 35 U.S.C. 154(b) by 180 days.

(21) Appl. No.: 09/980,064

(22) PCT Filed: May 31, 2000

(86) PCT No.: PCT/EP00/05005

§ 371 (c)(1),
(2), (4) Date: Mar. 27, 2002

(87) PCT Pub. No.: WO00/73464

PCT Pub. Date: Dec. 7, 2000

(30) Foreign Application Priority Data

Jun. 1, 1999 (DE) .......................................... 199 25 235

(51) Int. Cl.⁷ ............................................... A61K 39/12
(52) U.S. Cl. ................................ 424/204.1; 424/186.1; 530/300; 536/23.72
(58) Field of Search ........................... 424/204.1, 186.1; 530/300; 536/23.72

(56) References Cited

U.S. PATENT DOCUMENTS

| | | | |
|---|---|---|---|
| 4,777,239 | A | 10/1988 | Schoolnik et al. |
| 5,415,995 | A | 5/1995 | Schoolnik et al. |
| 5,547,846 | A | 8/1996 | Bartsch et al. |
| 5,629,161 | A | 5/1997 | Müller et al. |
| 5,662,907 | A | 9/1997 | Kubo et al. |
| 5,747,269 | A | 5/1998 | Rammensee et al. |
| 6,025,163 | A | 2/2000 | Shamanin et al. |
| 6,183,746 | B1 | 2/2001 | Urban et al. |

FOREIGN PATENT DOCUMENTS

| | | |
|---|---|---|
| CA | 2140591 | 7/1995 |
| EP | 0 375 555 | 6/1990 |
| EP | 0 386 734 | 9/1990 |
| EP | 0 451 550 A2 | 10/1991 |
| GB | 2 279 651 | 1/1995 |
| WO | WO 91/18294 | 11/1991 |
| WO | WO 92/05248 | 4/1992 |
| WO | WO 92/10513 | 6/1992 |
| WO | WO 93/02184 | 2/1993 |
| WO | WO 93/20844 | 10/1993 |
| WO | WO 93/22338 | 11/1993 |
| WO | WO 94/05792 | 3/1994 |
| WO | WO 94/20137 | 9/1994 |
| WO | WO 95/01374 | 1/1995 |
| WO | WO 96/11272 | 4/1996 |
| WO | WO 96/33737 | 10/1996 |
| WO | WO 98/05790 | 2/1998 |
| WO | WO 98/23752 | 6/1998 |
| WO | WO 99/03885 | 1/1999 |
| WO | WO 99/18220 | 4/1999 |
| WO | WO 99/65522 | 12/1999 |

OTHER PUBLICATIONS

Altman et al., "Phenotypic Analysis of Antigen–Specific T Lymphocytes," *Science* 274:94–96 (1996).
Baker et al., "Structures of Bovine and Human Papillomaviruses," *Biophys. J.* 60:1445–1456 (1991).
De Bruijn et al., "Mechanisms of Induction of Primary Virus–Specific Cytotoxic T Lymphocyte Responses," *Eur. J. Immunol.* 22:3013–3020 (1992).
De Bruijn et al., "Peptide Loading of Empty Major Histocompatibility Complex Molecules on RMA–S Cells Allows the Induction of Primary Cytotoxic T Lymphocyte Responses," *Eur. J. Immunol.* 21:2963–2970 (1991).
De Gruijl et al., "Immune Responses Against Huamn Papillomavirus (HPV) Type 16 Virus–Like Particles in a Cohort Study of Women with Cervical Intraepithelial Neoplasia 1 . Differential T–Helper and IgG Responses in Relation to HPV Infection and Disease Outcome," *Journal of General Virology* 80:399–408 (1999).
Dunbar et al., "Direct isolation, Phenotyping and Cloning of Low–Frequency Antigen–Specific Cytotoxic T Lymphocytes From Peripheral Blood," *Current Biology* 8:413–416 (1998).
Feltkamp et al., "vaccination with a Cytotoxic T Lymphocyte–Containing Peptide Protects Aganist a Tumor Induced by Human Papillomavirus Type 16–Transformed Cells," *Eur. J. Immunol.* 23:2242–2249 (1993).
Gossen et al., "Inducible Gene Expression Systems for High Eukaryotic Cells," *Current Opinion in Biotechnology* 5:516–520 (1994).
Heino et al., "Human Papillomavirus Type 16 Capsids Expose Multipe Type–Restricted and Type–Common Antigenic Epitopes, " *Journal of General Virology* 76:1141–1153 (1995).
Kast et al., "Role of HLA–A Motifs in Identification of Potential CTL Epitopes in Human Papillomavirus Type 16 E6 and E7 Proteins," *Journal of Immunology* 152:3904–3912 (1994).
Krchnak et al., "Synthetic Peptides Derived From E7 Region of Human Papillomavirus Type 16 used as Antigens in ELISA," *Journal of General Virology* 71:2719–2724 (1990).
Müller et al., "Identification of Seroreactive Regions of the Human Papillomavirus Type 16 Proteins E4, E6, E7, and L1," *Journal of General Virology* 71:2709–2717 (1990).

(Continued)

Primary Examiner—Ali R. Salimi
(74) Attorney, Agent, or Firm—Clark & Elbing LLP

(57) ABSTRACT

The present invention relates to a papillomavirus T-cell epitope having an amino acid sequence AQIFNKPYW, AGVDNRECI and/or to a functionally active variant thereof, also to their use in diagnostics and therapy.

1 Claim, 5 Drawing Sheets

OTHER PUBLICATIONS

Müller et al., "Chimeric Papillomavirus–Like Particles," *Virology* 234:93–111 (1997).

Nieland et al., "Chimeric Papillomavirus Virus–Like Particles Induce a Murine Self–Antigen–Specific Protective and Therapeutic Antitumor Immune Response," *Journal of Cellular Biochemistry* 71:145–152 (1999).

Parker et al., "Scheme for Ranking Potential HLA–A2 Binding Peptides Based on Independent Binding of Individual Peptide Side–Chains," *Journal of Immunology* 152:163–175 (1994).

Peng et al., "Papillomavirus Virus–Like Particles Can Deliver Defined CTL Epitopes to the MHC Class I Pathway," *Virology* 240:147–157 (1998).

Rudolf et al., "Induction of HPV16 Capsid Protein–Specific Human T Cell Responses by Virus–Like Particles," *Biol. Chem.* 380:335–340 (1999).

Schäfer et al., "Immune Response to Human Papillomavirus 16 L1E7 Chimeric Virus–Like Particles: Induction of Cytotoxic T Cells and Specific Tumor Protection," *Int. J. Cancer* 81:881–888 (1999).

Sijts et al., "Cytotoxic T Lymphocytes Aganist the Antigen–Processing–Defective RMA–S Tumor Cell Line," *Eur. J. Immunol.* 22:1639–1642 (1992).

Sijts et al., "Immunodominant Mink Cell Focus–Inducing Murine Leukemia Virus (MuLV)–Encoded CTL Epitope, Identified by Its MHC Class I–Binding Motif, Explains MuLV–Type Specificity of MCF–Directed Cytotoxic T Lymphocytes," *Journal of Immunology* 152:106–116 (1994).

Tsukui et al., "Interleukin 2 Production in Vitro by Peripheral Lymphocytes in Response to Human Papillomavirus–Derived Peptides: Correlation with Cervical Pathology," *Cancer Research* 56:3967–3974 (1996).

Zhou et al, "Definition of Linear Antigenic Regions of the HPV 16 L1 Capsid Protein Using Synthetic Virion–Like Particles," *Virology* 189:592–599 (1992).

Zwicker et al., "Cell–Cycle Regulation of Gene Expression by Transcriptional Repression," *TIG* 13:3–6 91997).

Chan et al., "Phylogenetic Analysis of 48 Papillomavirus Types and 28 Subtypes and Variants: A Showcase for the Molecular Evolution of DNA Viruses," *Journal of Virology* 66:5714–5725 (1992).

SEQUENCE LISTING

<160> NUMBER OF SEQ ID NOS: 17

<210> SEQ ID NO 1
<211> LENGTH: 9
<212> TYPE: PRT
<213> ORGANISM: Human papillomavirus type 16

```
<400> SEQUENCE: 1

Ala Gln Ile Phe Asn Lys Pro Tyr Trp
1               5

<210> SEQ ID NO 2
<211> LENGTH: 9
<212> TYPE: PRT
<213> ORGANISM: Human papillomavirus type 16

<400> SEQUENCE: 2

Ala Gly Val Asp Asn Arg Glu Cys Ile
1               5

<210> SEQ ID NO 3
<211> LENGTH: 9
<212> TYPE: PRT
<213> ORGANISM: Influenza Virus Type A

<400> SEQUENCE: 3

Ala Ser Asn Glu Asn Met Glu Thr Met
1               5

<210> SEQ ID NO 4
<211> LENGTH: 8
<212> TYPE: PRT
<213> ORGANISM: Human papillomavirus type 16

<400> SEQUENCE: 4

Gly Ala Met Asp Phe Thr Thr Leu
1               5

<210> SEQ ID NO 5
<211> LENGTH: 8
<212> TYPE: PRT
<213> ORGANISM: Human papillomavirus type 16

<400> SEQUENCE: 5

Gly Asp Ser Leu Phe Phe Tyr Leu
1               5

<210> SEQ ID NO 6
<211> LENGTH: 8
<212> TYPE: PRT
<213> ORGANISM: Human papillomavirus type 16

<400> SEQUENCE: 6

Met Gln Val Thr Phe Ile Tyr Ile
1               5

<210> SEQ ID NO 7
<211> LENGTH: 8
<212> TYPE: PRT
<213> ORGANISM: Human papillomavirus type 16

<400> SEQUENCE: 7

Val Tyr His Ile Phe Phe Asn Met
1               5

<210> SEQ ID NO 8
<211> LENGTH: 8
<212> TYPE: PRT
<213> ORGANISM: Human papillomavirus type 16

<400> SEQUENCE: 8
```

```
Val His Thr Gly Phe Gly Ala Met
1               5

<210> SEQ ID NO 9
<211> LENGTH: 8
<212> TYPE: PRT
<213> ORGANISM: Human papillomavirus virus

<400> SEQUENCE: 9

Lys Tyr Pro Asp Tyr Ile Lys Met
1               5

<210> SEQ ID NO 10
<211> LENGTH: 8
<212> TYPE: PRT
<213> ORGANISM: Human papillomavirus type 16

<400> SEQUENCE: 10

Val Thr Phe Ile Tyr Ile Leu Val
1               5

<210> SEQ ID NO 11
<211> LENGTH: 8
<212> TYPE: PRT
<213> ORGANISM: Human papillomavirus type 16

<400> SEQUENCE: 11

Leu Glu Asp Thr Tyr Arg Phe Val
1               5

<210> SEQ ID NO 12
<211> LENGTH: 8
<212> TYPE: PRT
<213> ORGANISM: Human papillomavirus type 16

<400> SEQUENCE: 12

Gly Asn Gln Leu Phe Val Thr Val
1               5

<210> SEQ ID NO 13
<211> LENGTH: 8
<212> TYPE: PRT
<213> ORGANISM: Human papillomavirus type 16

<400> SEQUENCE: 13

Lys Lys Tyr Thr Phe Val Thr Val
1               5

<210> SEQ ID NO 14
<211> LENGTH: 8
<212> TYPE: PRT
<213> ORGANISM: Human papillomavirus type 16

<400> SEQUENCE: 14

Glu Asn Asp Val Asn Tyr His Ile
1               5

<210> SEQ ID NO 15
<211> LENGTH: 9
<212> TYPE: PRT
<213> ORGANISM: Human papillomavirus type 16

<400> SEQUENCE: 15

Ala Gly Val Asp Asn Arg Glu Cys Ile
```

-continued

```
1               5

<210> SEQ ID NO 16
<211> LENGTH: 10
<212> TYPE: PRT
<213> ORGANISM: Human papillomavirus type 16

<400> SEQUENCE: 16

Thr Val Gly Glu Asn Val Pro Asp Asp Leu
 1               5                  10

<210> SEQ ID NO 17
<211> LENGTH: 10
<212> TYPE: PRT
<213> ORGANISM: Human papillomavirus type 16

<400> SEQUENCE: 17

Tyr Lys Asn Thr Asn Phe Lys Glu Tyr Leu
 1               5                  10
```

CYTOTOXIC T-CELL EPITOPES OF THE PAPILLOMAVIRUS L1-PROTEIN AND USE THEREOF IN DIAGNOSTICS AND THERAPY

This application is the U.S. National Stage of International Application No. PCT/EP2000/05005, filed May 31, 2000, which claims the benefit of German Application No. 19925235.1, filed Jun. 1, 1999, all of which are hereby incorporated by reference.

The present invention relates to a papillomavirus T-cell epitope having an amino acid sequence AQIFNKPYW, AGVDNRECI and/or to a functionally active variant thereof, and also to its use in diagnostics and therapy.

The papillomaviruses, also called wart viruses, are double-stranded DNA viruses with a genome size of about 8000 base pairs and an icosahedral capsid of approx. 55 nm in diameter. Up until now, more than 100 different human-pathogenic papillomavirus types (HPV) are known, some of which, for example HPV-16, HPV-18, HPV-31, HPV-33, HPV-39, HPV-45, HPV-52 or HPV-58, may cause malignant tumors and others, for example HPV-6, HPV-11 or HPV-42, may cause benign tumors.

The papillomavirus genome can be divided into three parts: the first part relates to a noncoding region containing regulatory elements for virus transcription and replication. The second region, the "E" (early) region, contains various protein-encoding sections E1–E7 of which, for example, the E6 and E7 proteins are responsible for transformation of epithelial cells and the E1 protein controls the DNA copy number. The E6 and E7 regions are "oncogenes" which are also expressed in malignantly degenerate cells. The third region, also called L (late) region, contains two protein-encoding sections L1 and L2 which code for structural components of the virus capsid. Over 90% of the L protein is present in the viral capsid, the L1:L2 ratio generally being 30:1. In accordance with the present invention, the term L1 protein means the main capsid protein of papillomaviruses (Baker T. et al. (1991) Biophys. J. 60, 1445).

In over 50% of cases, HPV-16 is connected with cervical cancer (carcinoma of the cervix). HPV-16 is the main risk factor for the formation of cervical neoplasms. The immune system plays an important part in the progress of the disease. Thus, cellular immune responses and in particular antigen-specific T lymphocytes are presumably important for the defense mechanism. It has furthermore been found that in high-grade malignant cervical intraepithelial neoplasms (CIN II/III) and cervical tumors the E7 gene is expressed constitutively in all layers of the infected epithelium. The E7 protein in particular is therefore considered as a potential tumor antigen and as a target molecule for activated T cells (see, for example, WO 93/20844). The E7-induced cellular immune response in the patient, however, is apparently not strong enough to influence the course of the disease. The immune response may possibly be amplified by suitable vaccines.

It has been possible to show that expression of the L1 gene and/or coexpression of the L1 and L2 genes can lead to the formation of capsomers, stable capsomers, capsids or virus-like particles (VLPs) (see, for example, WO 93/02184, WO 94/20137 or WO 94/05792). Capsomers mean an oligomeric configuration which is composed of five L1 proteins. The capsomer is the basic building block of which viral capsids are composed. Stable capsomers mean capsomers which are incapable of assembling to form capsids. Capsids mean the papillomavirus coat which is, for example, composed of 72 capsomers (Baker T. et al. (1991) Biophys. J. 60, 1445). VLP means a capsid which is morphologically and in its antigenicity identical to an intact virus. It was possible to use the VLPs in various animal systems for causing a humoral immune response characterized by the formation of neutralizing antibodies. The formation of virus-neutralizing antibodies against L1 and/or L2 protein, however, is of relatively low clinical importance if the virus infection has already taken place, since for the elimination of virus-infected cells a virus-specific cytotoxic T-cell (CTL) response rather than antibodies seems to be necessary. And, although VLPs are capable of causing a cytotoxic T-cell response, an immune response exclusively directed against the capsid proteins L1 and/or L2 appears unsuitable for controlling a tumor caused by papillomaviruses.

Therefore, "chimeric papillomavirus-like particles" (CVLPs) which comprise a fusion protein of the capsid protein L1 and the potential tumor antigen E7 (WO 96/11272 and Muller, M. et al. (1997) Virology, 234, 93) have been developed. The CVLPs caused only to a small extent a humoral immune response directed against the E7 protein (Muller, M. et al. (1997), supra). Some of the CVLPs tested, however, do indeed induce the desired E7-specific cytotoxic T-cell response in mice (see also Peng S. et al. (1998) Virology 240, 147–57). As a result, CVLPs are of interest both for the development of a vaccine and for the treatment of already established infections and tumors resulting therefrom, since the E7 tumor cell peptides presented via MHC molecules of class I would represent target molecules of cytotoxic T cells.

A vaccine comprising CVLPs is based on the principle of the CVLPs pseudo-infecting cells. This means that CVLPs and viruses alike get into the cell, are processed there to peptides, and the peptides are loaded onto MHC class I and II molecules and finally presented to CD8- or CD4-positive T cells. As a consequence of this stimulation, CD8 cells may differentiate into cytotoxic T cells and then cause a cellular immune response, whereas CD4 cells develop into T helper cells and stimulate B cells to give a humoral or CD8-positive T cells to give a cytotoxic immune response and may themselves induce lysis of infected cells.

Small peptides may bind to MHC class I molecules already on the cell surface and then stimulate without further processing CD8- or CD4-positive cells to give a cellular immune response. However, a particular peptide can be bound only by particular MHC molecules. Due to the large polymorphism of MHC molecules in natural populations, a particular peptide can therefore be bound and presented only by a small part of a population. In accordance with the present invention, presentation means binding of a peptide or protein fragment to an MHC molecule, it being possible for said binding to take place, for example, in the endoplasmic reticulum, the extracellular space, the endosomes, proendosomes, lysosomes or protysosomes, and said MHC molecule-peptide complex then being bound on the extracellular side of the cell membrane so that it can be recognized specifically by immune cells.

Since CVLPs cause both a cellular and a humoral immune response and are not MHC-restricted, this technology is generally suitable for the development of vaccines, since an L1 portion provides the ability to form particles and an additional antigen portion is fused to said L1 portion.

For the development of CVLPs of this kind it is absolutely necessary to have a functional assay system available which can be used to study directly the immunogenicity of CVLPs. Such an assay system should have the property that CVLPs with different antigen proportions can be studied by using the same assay system. Since the cellular immune response is of crucial importance for immunological therapies of tumors or viral diseases, the object arose to make it possible to measure the cellular immune response caused by CVLPs.

This object was achieved by identifying T-cell epitopes which in connection with MHC molecules, and in a particular embodiment with (H2-$D^b$) MHC molecules, cause, for example, a cytotoxic T-cell response in vivo and in vitro. Said peptides preferably have the sequence AQIFNKPYW or AGVDNRECI. These sequences are part of the L1 peptide of HPV16. They include the amino acid regions 330 to 338 (L1$_{330-338}$) and 165 to 173 (L1$_{165-173}$).

The present invention therefore relates to a T-cell epitope having an amino acid sequence AQIFNKPYW, AGVDNRECI and/or to a functionally active variant thereof.

A functionally active variant of AQIFNKPYW (SEQ ID NO: 1) or AGVDNRECI (SEQ ID NO: 2) means a T-cell epitope which, in a T-cell cytotoxicity assay system (see, for example, Examples 2–5 of the present invention), has a cytotoxicity which, compared to the cytotoxicity of AQIFNKPYW (SEQ ID NO: 1) or AGVDNRECI (SEQ ID NO: 2), corresponds to at least the sum of the average of the negative controls and three times the standard deviation, preferably of at least approx. 30%, in particular at least approx. 50% and particularly preferably of at least approx. 80%.

An example of a preferred variant is a T-cell epitope having a sequence homology to AQIFNKPYW (SEQ ID NO: 1) or AGVDNRECI (SEQ ID NO: 2) of at least approx. 65%, preferably at least approx. 75% and in particular at least approx. 85% at the amino acid level. Other preferred variants are also T-cell epitopes which are structurally homologous to AQIFNKPYW (SEQ ID NO: 1) or AGVDNRECI (SEQ ID NO: 2). Such epitopes may be found by generating specific T-cells against the T-cell epitopes AQIFNKPYW (SEQ ID NO: 1), AGVDNRECI (SEQ ID NO: 2) (DeBruijn M. L. et al. (1991) Eur. J. Immunol. 21, 2963–70; and DeBruijn M. L. (1992) Eur. J. Immunol. 22, 3013–20) and assaying, for example, synthetically produced peptides of choice for recognition by the peptide-specific T cells (see examples). The T-cell epitopes in particular mean cytotoxic T-cell epitopes. However, noncytotoxic T cells are also known which can likewise recognize MHC I molecules so that the present invention also includes noncytotoxic T-cell epitopes as variant.

Another embodiment of the present invention is a T-cell epitope which is part of a compound, the compound not being a naturally occurring L1 protein of a papillomavirus and not being an exclusively N-terminal or exclusively C-terminal deletion mutant of a naturally occurring L1 protein of a papillomavirus. In a particular embodiment, a T-cell epitope having an amino acid sequence AQIFNKPYW (SEQ ID NO: 1), AGVDNRECI (SEQ ID NO: 2), and/or a functionally active variant may be contained in an L1 protein of a different papillomavirus or in a chimeric L1 protein, for example an HPV18L1E7 fusion protein. Such a compound of the invention may have the ability to form CVLPs.

As part of a compound, said T-cell epitope may preferably be a polypeptide which preferably contains further amino acid sequences, and in particular a fusion protein. In particular, the compound may be a polypeptide of at least approx. 50 amino acids, preferably of at least approx. 35 amino acids, in particular of at least approx. 20 amino acids and particularly preferably of at least approx. 9 amino acids, in length.

In order to detect the compound or to modify its T-cell binding activity, said compound may contain a chemical, radioactive isotope, nonradioactive isotope and/or fluorescent label of the T-cell epitope and/or of said fusion protein.

Examples of chemical substances known to the skilled worker, which are suitable for chemical labeling according to the invention, are: biotin, FITC (fluorescein isothiocyanate) or streptavidin.

In a possible embodiment a peptide is modified such that it contains at least one lysine. In a manner known to the skilled worker biotin or FITC (fluorescein isothiocyanate) is coupled to said lysine. A peptide modified in this way is bound to an appropriate MHC molecule or to a cell containing appropriate MHC molecules. The peptide may then be detected via labeled avidin or streptavidin or directly via FITC fluorescence.

Examples of isotopes known to the skilled worker, which are suitable for radioactive isotope labeling according to the invention are: $^3$H, $^{125}$I, $^{131}$I, $^{32}$P, $^{33}$P or $^{14}$C.

Examples of isotopes known to the skilled worker, which are suitable for nonradioactive isotope labeling according to the invention are: $^2$H, or $^{13}$C.

Examples of fluorescent substances known to the skilled worker, which are suitable for fluorescence labeling according to the invention are: $^{152}$Eu, fluorescein isothiocyanate, rhodamine, phycoerythrin, phycocyanin, allophycocyanin, o-phtaldehyde or fluorescamine.

Further label not listed here, which may also be used for labeling in accordance with this invention, are known to the skilled worker.

Examples of inventive chemical modifications known to the skilled worker are the transfer of acetyl, phosphate and/or monosaccharide groups.

Inventive polypeptides of approx. 50 amino acids in length may be prepared, for example, by chemical peptide synthesis. Longer polypeptides are preferably generated by genetic engineering. The present invention therefore further relates to a nucleic acid construct for expressing said T-cell epitope or compounds containing the following components: (a) at least one regulatory element and (b) at least one nucleic acid coding for an amino acid sequence of the compound of the invention. Said nucleic acid construct is preferably made of DNA or RNA. Suitable regulatory elements allow, for example, constitutive, regulatable, tissue-specific, cell cycle-specific or metabolically specific expression in eukaryotic cells or constitutive, metabolically specific or regulatable expression in prokaryotic cells. Regulatable elements according to the present invention are promoters, activator sequences, enhancers, silencers, and/or repressor sequences.

Examples of suitable regulatable elements which make constitutive expression in eukaryotes possible are promoters recognized by RNA polymerase III or viral promoters such as CMV enhancer, CMV promoter, SV40 promoter and viral promoter and activator sequences derived, for example, from HBV, HCV, HSV, HPV, EBV, HTLV or HIV.

Examples of regulatable elements which make regulatable expression in eukaryotes possible are the tetracyclin operator in combination with a corresponding repressor (Gossen M. et al (1994) Curr. Opin. Biotechnol. 5, 516–20).

Examples of regulatable elements which make tissue-specific expression in eukaryotes possible are promoters or activator sequences from promoters or enhancers of those genes coding for proteins which are expressed only in particular cell types.

Examples of regulatable elements which make cell cycle-specific expression in eukaryotes possible are the promoters of the following genes: cdc25C, cyclin A, cyclin E, cdc2, E2F, B-myb or DHFR (Zwicker J. and Muller R. (1997) Trends Genet. 13, 3–6).

Examples of regulatable elements which make metabolically specific expression in eukaryotes possible are promoters regulated by hypoxia, by glucose deficiency, by phosphate concentration or by heat shock.

In order to make it possible to introduce said nucleic acid and thus express the polypeptide in a eukaryotic or prokaryotic cell by transfection, transformation or infection, the nucleic acid may be present as plasmid, or as part of a viral or nonviral vector. The present invention therefore further relates to a vector, in particular an expression vector which contains a nucleic acid coding for a polypeptide of the invention. Viral vectors particularly suitable here are: baculo viruses, vaccinia viruses, adenoviruses, adeno-associated viruses and herpes viruses. Nonviral vectors particularly suitable here are: virosomes, liposomes, cationic lipids or polylysine-conjugated DNA.

The present invention further relates to a cell containing, preferably presenting, at least one T-cell epitope. In a particular embodiment, the cell is transfected, transformed or infected by one of the vectors mentioned. This cell expresses the polypeptide of the invention under conditions known to a skilled worker which lead to activation of the regulatable elements used in each case. The polypeptide can then be isolated from said cell and purified, for example by using one of the abovementioned labels. Cells which are suitable for the preparation by genetic engineering and subsequent purification of the expressed compounds of the invention are prokaryotic and eukaryotic cells, in particular bacteria cells such as, for example, *E. coli*, yeast cells such as, for example, *S. cerevisiae*, insect cells such as, for example, *Spodoptera frugiperda* cells (Sf-9) or Trichoplusia ni cells or mammalian cells such as, for example, COS cells or HeLa cells.

A particular embodiment is using the cell itself which expresses the polypeptide of the invention, and, in a particularly preferred embodiment, the cell presents parts of the polypeptide of the invention via MHC-1 molecules on the cell surface. Suitable cells for preparing the cell of the invention are antigen-presenting cells such as, for example, B cells, macrophages, dendritic cells, embryonic cells or fibroblasts, in a preferred embodiment B16F10, B6, C3, EL4, RMA or RMA-S cells. The cells of the invention which present a polypeptide containing a T-cell epitope may be employed as target cells for restimulating immune cells, in particular T cells, and/or for measuring T-cell activation. A target cell means in accordance with the present invention a cell which presents a T-cell epitope via MHC molecules and thus specifically causes T-cell activation, in particular a cytotoxic T-cell reaction against the cell.

Furthermore, the T-cell epitope-containing compound may be part of a complex which is characterized by the compound being linked covalently or by hydrophobic interactions, ionic binding or hydrogen bonds to at least one further species such as peptides, proteins, peptoids, linear or branched oligo or polysaccharides and nucleic acids.

The present invention therefore relates to a complex containing a T-cell epitope or a compound and at least one further compound. In a preferred embodiment, the polypeptide is linked to MHC class I molecules, preferably as H2-D b tetramer. Particular preference is given to human or murine MHC class I molecules, in particular an MHC class I molecule derived from C57B1/6 mice. Using the technique by Altman J. D. et al. (1996, Science 274, 94–6) it is possible, for example, to prepare H2-$D^b$ tetramers with the appropriate bound peptides which are capable of binding to T-cell receptors of peptide-specific cytotoxic T cells.

Another embodiment is immobilization of the compound of the invention or of said complex to support materials. Examples of suitable support materials are ceramic, metal, in particular noble metal, glasses, plastics, crystalline materials or thin layers of this support, in particular of said materials, or (bio)molecular filaments such as cellulose or structural proteins.

In order to purify the complex of the invention, a component of the complex may additionally also contain a protein tag. Protein tags of the invention allow, for example, high-affinity absorption to a matrix, stringent washing with suitable buffers with negligible elution of the complex and subsequent specific elution of the absorbed complex. Examples of protein tags known to the skilled worker are an N- or C-terminal $(HIS)_6$ tag, a myc tag, a FLAG tag, a hemagglutinin tag, glutathione transferase (GST) tag, intein with chitin-binding affinity tag or maltose-binding protein (MBP) tag. The protein tags of the invention may be located N-terminally, C-terminally and/or internally.

The present invention also relates to a method for in vitro detection of the activation of T cells by at least one compound containing a T-cell epitope. A method of this kind preferably comprises three steps:

a) In a first step, cells are stimulated by at least one compounds containing a T-cell epitope. This compound may be at least one inventive compound containing a T-cell epitope, at least one inventive complex containing a T-cell epitope, at least one capsomer, at least one stable capsomer, at least one VLP, at least one CVLP, and/or at least one virus. In a preferred embodiment, immune cells are stimulated by incubation with CVLPs. This stimulation may be carried out, for example, in the form of a vaccination or by incubating immune cells with CVLPs in vitro. Immune cells stimulated in this way are obtained, for example, after a vaccination from the spleen, from lymph nodes or from the blood, and/or are cultured.

b) In a second step, the cells are incubated with at least one T-cell epitope of the invention, at least one inventive compound containing a T-cell epitope, at least one target cell presenting a T-cell epitope and/or with at least one complex of the invention.

c) In a third step, T-cell activation is determined. Examples of methods suitable for this are detection of cytokine production or secretion by the T cells, of the surface molecule expression on T cells, of target cell lysis or of cell proliferation. Examples of methods suitable for this are a cytokinassay (Chapter 6.2 to 6.24 in Current Protocols in Immunology (1999), edited by Coligan J. E., Kruisbeek A. M., Margulies D. H., Shevach E. M. and Strober W., John Wiley & Sons), ELISPOT (Chapter 6.19 in Current Protocols in Immunology, supra), a $^{51}Cr$ release assay (Chapter 3.11 in Current Protocols in Immunology, supra) or detection of proliferation (Chapter 3.12 in Current Protocols in Immunology, supra). Depending on the method used, it is in this connection also possible to distinguish between the immune cells such as cytotoxic T cells, T helper cells, B cells, NK cells, and other cells. The use of inventive compounds, complexes, and/or cells containing the labels of the invention allows detection of T cells recognizing the T-cell epitope via detection of the binding of labeled compounds, complexes and/or cells to the T-cells. In a preferred embodiment, binding of inventive MHC-polypeptide complexes to the surface of T cells is detected. This may be carried out such that the MHC complexes are labeled themselves, for example fluorescently labeled, or that, in a further step, an MHC-specific, labeled, for example fluorescently labeled, antibody is used in order to detect in turn the MHC complexes. The fluorescent label of the T cells can then be measured and evaluated, for example, in a fluorescence-activated cell sorter (FACS). Another possible way of detecting binding of the complexes to the T cells is again measuring T-cell activation (cytokine assay, Elispot, $^{51}$Cr release assay, proliferation, see above). However, this requires simultaneous stimulation of coreceptors (e.g. CD28), for example by coreceptor-specific antibodies (anti-CD28) and/or other unspecific activators (IL-2).

The present invention also relates to a method containing an additional step a') which is introduced after step a).

a') In this additional step a') which follows step a), the isolated or cultured cells are are cocultured with at least one target cell loaded with an inventive compound containing a T-cell epitope, at least one inventive complex containing a T-cell epitope, at least one capsomer, at least one stable capsomer, at least one VLP, at least one CVLP and/or at least one virus, with at least one inventive complex containing a T-cell epitope, and/or at least one target cell presenting a T-cell epitope for at least approx. 12 days, in particular for approx. 5 days, prior to step b).

Coculturing means growing cells:

(i) in the presence of at least one target cell loaded with an inventive compound containing a T-cell epitope, at least one inventive complex containing a T-cell epitope, at least one capsomer, at least one stable capsomer, at least one VLP, at least one CVLP, and/or at least one virus, (ii) in the presence of at least one inventive complex containing a T-cell epitope, (iii) in the presence of at least one target cell presenting a T-cell epitope, in the same growth medium and the same tissue culture container.

The present invention further relates to a method for preparing a target cell presenting a T-cell epitope. It is possible here to load the target cell with combinations of different T-cell epitopes. In a preferred embodiment, the target cell is incubated with at least one compound containing a T-cell epitope and/or at least one complex containing a T-cell epitope. In a particularly preferred embodiment, the target cell is incubated in growth medium containing polypeptides of the invention or with MHC class I complexes with bound polypeptides of the invention. The MHC class I complexes may be present for example as H2-D$^b$ tetramers. In this connection, a tetramer normally binds four peptides. These can be identical or else represent different peptide species. In a further preferred embodiment, the target cell is transfected, transformed and/or infected with a nucleic acid and/or a vector. In a particularly preferred embodiment, the target cell is infected with a vaccinia virus vector. The method of the invention is carried out using antigen-presenting cells, for example B cells, macrophages, dendritic cells, embryonal cells or fibroblasts, and, in a preferred embodiment, using B16F10, B6, C3, EL4, RMA or RMA-S cells.

The CVLPs used contain a papillomavirus L1 protein or variants thereof, in particular HPV16 L1 protein and, but not necessarily, a protein heterologous to an L1 or variants thereof. The two proteins may be bound directly or indirectly. In accordance with the invention, directly bound means that the two proteins are covalently bound to one another, for example via a peptide bond or a disulfide bond. Indirectly bound means that the proteins are bound via noncovalent bonds, for example hydrophobic interactions, ionic bonds or hydrogen bonds. In a further embodiment, the CVLPs contain, in addition to L1 protein or variants thereof, a papillomavirus L2 protein.

Examples of a preferred embodiment of the L1 protein of the present invention are L1 proteins having one or more deletions, in particular a C-terminal deletion. A C-terminal deletion has the advantage that it is possible to increase the efficiency of virus-like particle formation, since the nuclear localization signal located at the C terminus is deleted. The C-terminal deletion is therefore preferably up to approx. 35 amino acids, in particular approx. 25 to approx. 35 amino acids, especially approx. 32 to approx. 34 amino acids. For example, a 32 amino acid long C-terminal deletion of the HPV16 L1 protein is sufficient in order to be able to increase the formation of virus-like particles at least approx. ten times. Furthermore, the L1 protein may carry one or more mutations or the L1 portion may be composed of L1 proteins of various papillomaviruses. A common characteristic of the L1 proteins of the invention is the fact that they permit the formation of VLPs or CVLPs and that they contain at least one T-cell epitope of the invention.

In a preferred embodiment, the L1 protein or variants thereof and the protein heterologous to L1 are a fusion protein. Heterologous proteins which are composed of a plurality of various proteins or parts thereof are also included. These may also be, for example, epitopes, in particular cytotoxic T-cell epitopes, of proteins. In this connection, epitopes in accordance with the invention may also be part of a synthetic polypeptide of approx. 50 amino acids, preferably of at least approx. 35 amino acids, in particular of at least approx. 20 amino acids and particularly preferably of at least approx. 9 amino acids, in length.

Preference is given to proteins heterologous to L1, which are derived from a viral protein, for example derived from HIV, HBV or HCV, preferably from papillomaviruses, in particular from human papillomaviruses.

In a preferred embodiment, said viral protein is a papillomavirus E protein, preferably an E6 and/or E7 protein. It is particularly preferred if the E protein is a deleted E protein, preferably a C-terminally deleted, in particular a C-terminally deleted E7 protein, since these constructs in connection with deleted L1 protein can form preferably virus-like particles. Particular preference is given to deletions of up to 55 amino acids, preferably approx. 5 to approx. 55 amino acids, in particular approx. 38 to approx. 55 amino acids.

In a further embodiment, the protein heterologous to L1 may originate from antigens of nonviral pathogens. Likewise, they may be derived from autoimmune antigens such as, for example, thyroglobulin, myelin basic protein or zona pellucida glycoprotein 3 (ZP$_3$), which are associated with particular autoimmune diseases such as, for example, thyroiditis, multiple sclerosis, oophoritis or rheumatoid arthritis. In a preferred embodiment, the protein heterologous to L1 originates from tumor antigens, preferably melanoma antigens such as MART, ovarian carcinoma antigens such as Her2 neu (c-erbB2), BCRA-1 or CA125, colon carcinoma antigens such as CA125 or breast carcinoma antigens such as Her2 neu (c-erbB2), BCRA-1, BCRA-2.

The present invention further relates to a method for in vitro detection of the activation of T cells which are obtained by preparation from samples. This method makes it possible to determine if a sample, for example a blood sample of a patient, or murine pancreas contain papillomavirus L1-protein-specific cytotoxic T cells. A detection method of this kind comprises the following steps:

a") In a first step, cells are obtained, for example by taking blood from a patient or by preparation, for example, of murine pancreas or lymph nodes. Subsequently, the cells are taken up in growth medium and cultured.

b) In a second step, cells are incubated with at least one target cell presenting a T-cell epitope or with at least one complex which comprises as a component a compound containing a T-cell epitope.

c) In a third step, T-cell activation is determined. Examples of methods suitable for this are detection of cytokine production or secretion by the T cells, of the surface molecule expression on T cells, of target cell lysis or of cell proliferation. Examples of methods suitable for this are a cytokinassay (Chapter 6.2 to 6.24 in Current Protocols in Immunology (1999), edited by Coligan J. E., Kruisbeek A. M., Margulies D. H., Shevach E. M. and Strober W., John Wiley & Sons), ELISPOT (Chapter 6.19 in Current Protocols in Immunology, supra), a $^{51}$Cr release assay (Chapter 3.11 in Current Protocols in Immunology, supra) or detection of proliferation (Chapter 3.12 in Current Protocols in Immunology, supra). Depending on the method used, it is in this connection also possible to distinguish between the immune cells such as cytotoxic T cells, T helper cells, B cells, NK cells, and other cells. The use of inventive compounds, complexes, and/or cells containing the labels of the invention allows detection of T cells recognizing the T-cell epitope via detection of the binding of labeled compounds, complexes and/or cells to the T cells. In a preferred embodiment, binding of inventive MHC-polypeptide complexes to the surface of T cells is detected. This may be carried out such that the MHC complexes are labeled themselves, for example fluorescently labeled, or that, in a further step, an MHC-specific, labeled, for example fluorescently labeled, antibody is used in order to detect in turn the MHC complexes. The fluorescent label of the T cells can then be measured and evaluated, for example, in a fluorescence-activated cell sorter (FACS). Another possibile way of detecting binding of the complexes to the T cells is again measuring T-cell activation (cytokine assay, Elispot, $^{51}$Cr release assay, proliferation, see above). However, this requires simultaneous stimulation of coreceptors (e.g. CD28), for example by coreceptor-specific antibodies (anti-CD28) and/or other unspecific activators (IL-2).

The present invention also relates to a method containing an additional step a') which is introduced after step a").

a') In this additional step a') which follows step a"), the isolated or cultured cells are cocultured with at least one target cell loaded with an inventive compound containing a T-cell epitope, at least one inventive complex containing a T-cell epitope, at least one capsomer, at least one stable capsomer, at least one VLP, at least one CVLP and/or at least one virus, with at least one inventive complex containing a T-cell epitope, and/or at least one target cell presenting a T-cell epitope for at least approx. 12 days, in particular for approx. 5 days, prior to step b).

Coculturing means growing cells:

(i) in the presence of at least one target cell loaded with an inventive compound containing a T-cell epitope, at least one inventive complex containing a T-cell epitope, at least one capsomer, at least one stable capsomer, at least one VLP, at least one CVLP, and/or at least one virus, (ii) in the presence of at least one inventive complex containing a T-cell epitope, (iii) in the presence of at least one target cell presenting a T-cell epitope, in the same growth medium and the same tissue culture container.

The invention further relates to an assay system (kit) for in vitro detection of the activation of T cells, comprising:

a) at least one T-cell epitope of the invention, at least one compound of the invention, at least one vector of the invention, at least one cell of the invention, and/or at least one complex of the invention, and b) effector cells of the immune system, preferably T cells, in particular cytotoxic T cells or T helper cells.

The invention further relates to an assay system (kit) for in vitro detection of the activation of T cells, comprising:

a) at least one T-cell epitope of the invention, at least one compound of the invention, at least one vector of the invention, at least one cell of the invention, and/or at least one complex of the invention, and b) effector cells of the immune system, preferably T cells, in particular cytotoxic T cells or T helper cells.

In a particular embodiment, the assay system is used for determining the L1 protein-specific cytotoxic T cells which are present, for example, in a patient's blood sample or in murine pancreas. In this case, the cells described in b) are control cells contained in the assay system, whose activation by the first kit component, the substances mentioned under a), serves as a standard. The activation observed in this reaction is compared with the T-cell activation of cells, which have been isolated from patients or mice, by kit component a).

In a further particular embodiment, the assay system is used, for example, for determining the L1 protein-specific antigenicity of a compound containing a T-cell epitope, a complex containing a T-cell epitope, a capsomer, a stable capsomer, a VLP, a CVLP and/or a virus. In this case, the substances described in a) are control substances whose activating effect on the second kit component, the cells mentioned under b), serves as a standard. The activation observed in this reaction is compared with the activating effect of a compound containing a T-cell epitope, a complex comprising a T-cell epitope, a capsomer, a stable capsomer, a VLP, a CVLP, and/or a virus on kit component b).

The invention further relates to the use of at least one T-cell epitope, at least one inventive compound containing a T-cell epitope, at least one inventive vector containing a nucleic acid coding for a T-cell epitope-containing compound, at least one inventive cell containing a T-cell epitope for, and/or at least one inventive complex containing a T-cell epitope for causing or detecting an immune response.

Suitable cells for immune cell stimulation in vitro as well as in vivo are in particular cells which present at least one of the molecules of the invention via their MHC class I molecules. Examples of cells suitable for antigen presentation are B cells, dendritic cells, macrophages, embryonic cells or fibroblasts which, by being cultured together with immune cells, can stimulate specific T cells.

In a particular embodiment, it is possible to use a compound of the invention, for example an HPV18 L1E7 fusion protein which additionally contains a T-cell epitope of the invention, for detecting an immune response. Such a compound of the invention may have the ability to form CVLPS.

The invention further relates to a medicament or diagnostic agent which contains at least one inventive compound containing a T-cell epitope, at least one vector containing a nucleic acid coding for a T-cell epitope-containing compound, at least one inventive cell containing a T-cell epitope, and/or at least one inventive complex containing a T-cell epitope and, if necessary, a pharmaceutically acceptable carrier.

Examples of carriers known to the skilled worker are glass, polystyrene, polypropylene, polyethylene, dextran, nylon, amylase, natural or modified cellulose, polyacrylamides, agarose, aluminum hydroxide or magnetite.

A medicament or diagnostic agent of the invention may be present in solution, bound to a solid matrix, and/or mixed with an adjuvant.

The medicament or diagnostic agent may be administered in different ways. Examples of administration forms known to the skilled worker are parenteral, local and/or systemic administration by, for example, oral, intranasal, intravenous, intramuscular, and/or topical administration. The preferred administration form is influenced, for example, by the natural path of infection of the particular papillomavirus infection. The amount administered depends on the age, weight and general state of health of the patient and the type of papillomavirus infection. The medicament or diagnostic agent may be administered in the form of capsules, a solution, suspension, elixir (for oral administration) or sterile solutions or suspensions (for parenteral or intranasal administration). An inert and immunologically acceptable carrier which may be used is, for example, a saline or phosphate-buffered saline. The medicament is administered in therapeutically effective amounts. These are amounts which are sufficient for causing a protective immunological response.

In a particular embodiment, it is possible to use a compound of the invention, for example an HPV18 L1E7 fusion protein which additionally contains a T-cell epitope of the invention, as medicament or diagnostic agent. Such a compound of the invention may have the ability to form CVLPs.

The figures and the following examples are intended to illustrate the invention in more detail, without restricting it.

EXAMPLES

1. Description of Starting Materials

The preparation of HPV16 L1$_{Ac}$E7$_{1-55}$ CVLPs was carried out according to the German patent application DE 198 12 941.6, (see also Muller M. et al. (1997) Virology 234, 93–111).

L1 VLPs (see Muller M. et al. (1997) Virology 234, 93–111)

C57B1/6 mice were obtained from Charles River Laboratories (Wilmington, Mass., USA).

MVA-L1$_{Ac}$ means a recombinant murine vaccinia virus expressing HPV16L1$_{Ac}$ in infected cells.

MVA-F6 is a vaccinia virus (control virus).

B6 cells means embryonic stem cells from a C57B1/6 mouse.

C3 cells means HPV16 and ras-transformed B6 embryonic cells (see Feltkamp M. C. et al. (1993) Eur. J. Immunol. 23, 2242–9).

RMA cells originate from a thymoma of a C57BL/6 mouse (see Ljunggren H. G. & Karre K. (1985) J. Exp. Med. 162, 1745–59).

RMA-S cells originate from a thymoma of a C57BL/6 mouse (see Ljunggren H. G. & Karre K. (1985) J. Exp. Med. 162, 1745–59). They have a defect in antigen processing-associated transport, which stops the loading of MHC-1 molecules in the endoplasmic reticulum. The unloaded MHC-1 molecules which are nevertheless present on the cell surface may be loaded, for example, by incubating the cells in peptide-containing media so that these cells are very suitable for presenting an antigen (see Powis S. J. et al. (1991) Nature 354, 528–31).

EL4 cells originate from a thymoma of a C57B1/6 mouse (see Shevach E. M. et al. (1972) J. Immunol. 108, 1146–51), for example ATCC TIB-49.

Cells were cultured in each case at 37° C. and 5% $CO_2$ in RPMI medium (Gibco BRL, Eggenstein Germany) with 10% fetal calf serum, kanamycin and ampicillin.

AM peptide means amino acids 366 to 374 of influenza nucleoprotein, sequence: ASNENMETM (see Townsend A. R. et al. (1986) Cell 44, =959–68) (SEQ ID NO: 3).

L1 peptides means HPV16-derived peptide of L1 main capsid protein.

Figure 1:
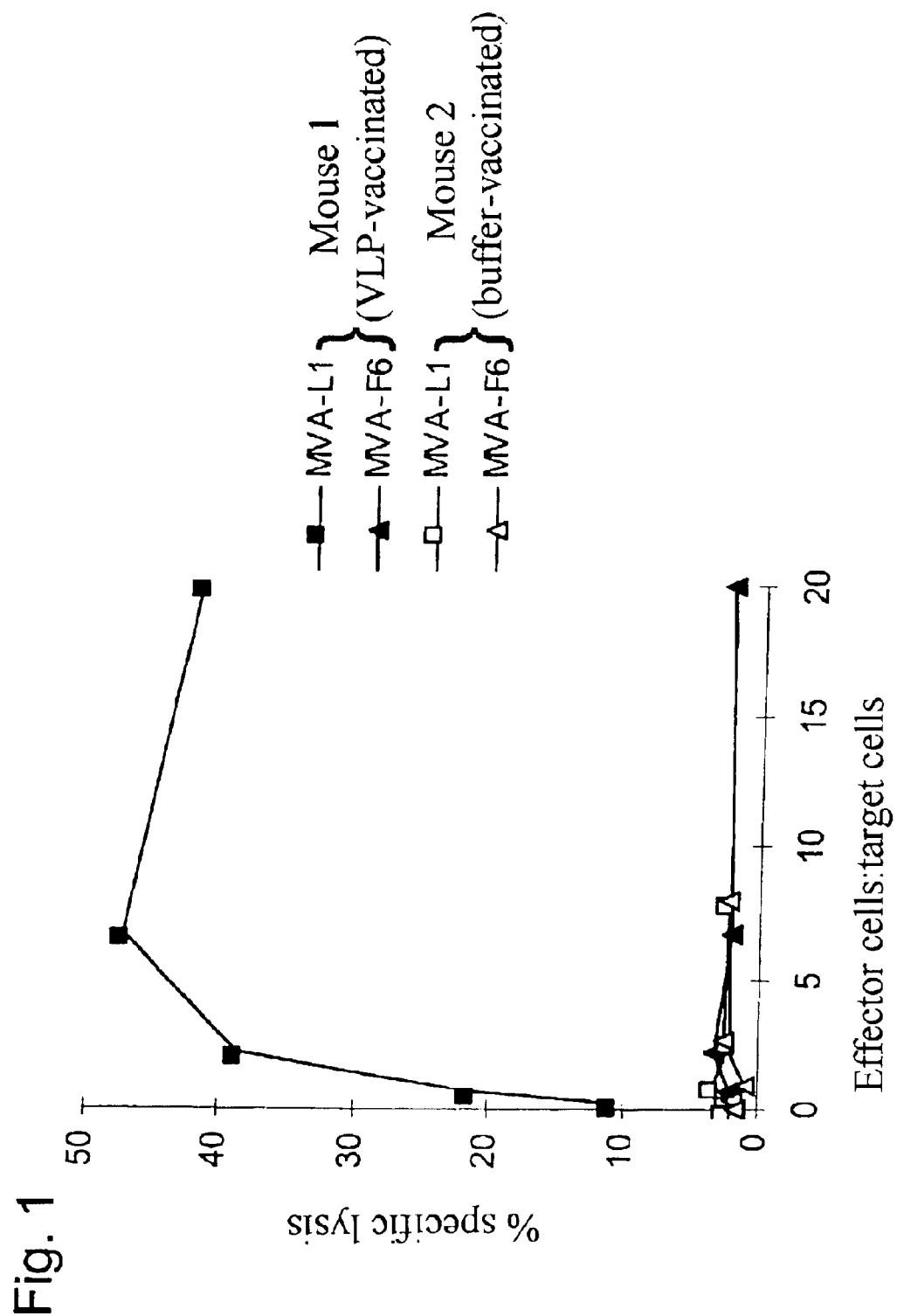
FIG. 1 shows the graphical analysis of the specific lysis of various murine B6 cells which had been infected with either MVA-L1$_{Ac}$ or MVA-F6 by spleen cells of mice which had been vaccinated either with VLPs or with buffer. The percentage of specific lysed cells is plotted as a function of the ratio of effector cells to target cells.

2. Induction of L1-Specific CTL After Immunization With L1 VLPs a) Immunization of Mice With VLPS:

Two C57B1/6 mice were immunized with 10 µg of L1 VLPs (mouse 1) or, as a control, with buffer (mouse 2). After 6 weeks, spleen cells were isolated.

b) Preparation of Antigen-Presenting Cells (Target Cells):

B6 cells were incubated with y interferon for 2.5 days, then infected with MVA-L1$_A$c viruses (MOI=5) for preparing antigen-presenting cells or with MVA-F6 for preparing control cells overnight and cultured for 16h. In a next step, the infected B6 cells were irradiated and thus prevented from further growth.

c) Restimulation of Isolated Spleen Cells:

The spleen cells from mouse 1 and 2 were in each case cultured together with the L1$_{Ac}$-expressing B6 cells which act as stimulator cells for T cells of the spleen cells for 5 days.

d) Cytotoxicity Assay of the Isolated Spleen Cells:

The stimulated spleen cells (effector cells) of mouse 1 (VLP-vaccinated) and 2 (buffer-vaccinated) were incubated either with MVA-L1$_A$c-infected or with MVA-F6-infected B6 cells (target cells) which had been incubated in each case beforehand in the presence of $^{51}$Cr at 37° C. for 1 h, in five different ratios of effector cells to target cells for 4 h. The specific lysis of the target cells was measured in a β counter by the release of radioactive $^{51}$Cr (see FIG. 1).

Result: Spleen cells of the L1-immunized mouse lysed the MVA-L1$_{Ac}$-infected target cells, but not the MVA-F6-infected target cells. The said spleen cells thus had specific cytotoxicity for the L1 protein. Control spleen cells originating from the buffer-vaccinated mouse showed no lytic activity towards the target cells.

3. Peptide-Specific Lysis of Target Cells by L1-Specific T Cells (VLP-Vaccinated Mice)

a) Preparation of Antigen-Presenting Cells:

During a one-hour incubation with $^{51}$Cr at 37° C., RMA-S cells were additionally incubated with a peptide (concentration 50 μM). The peptide used was either

Figure 2:
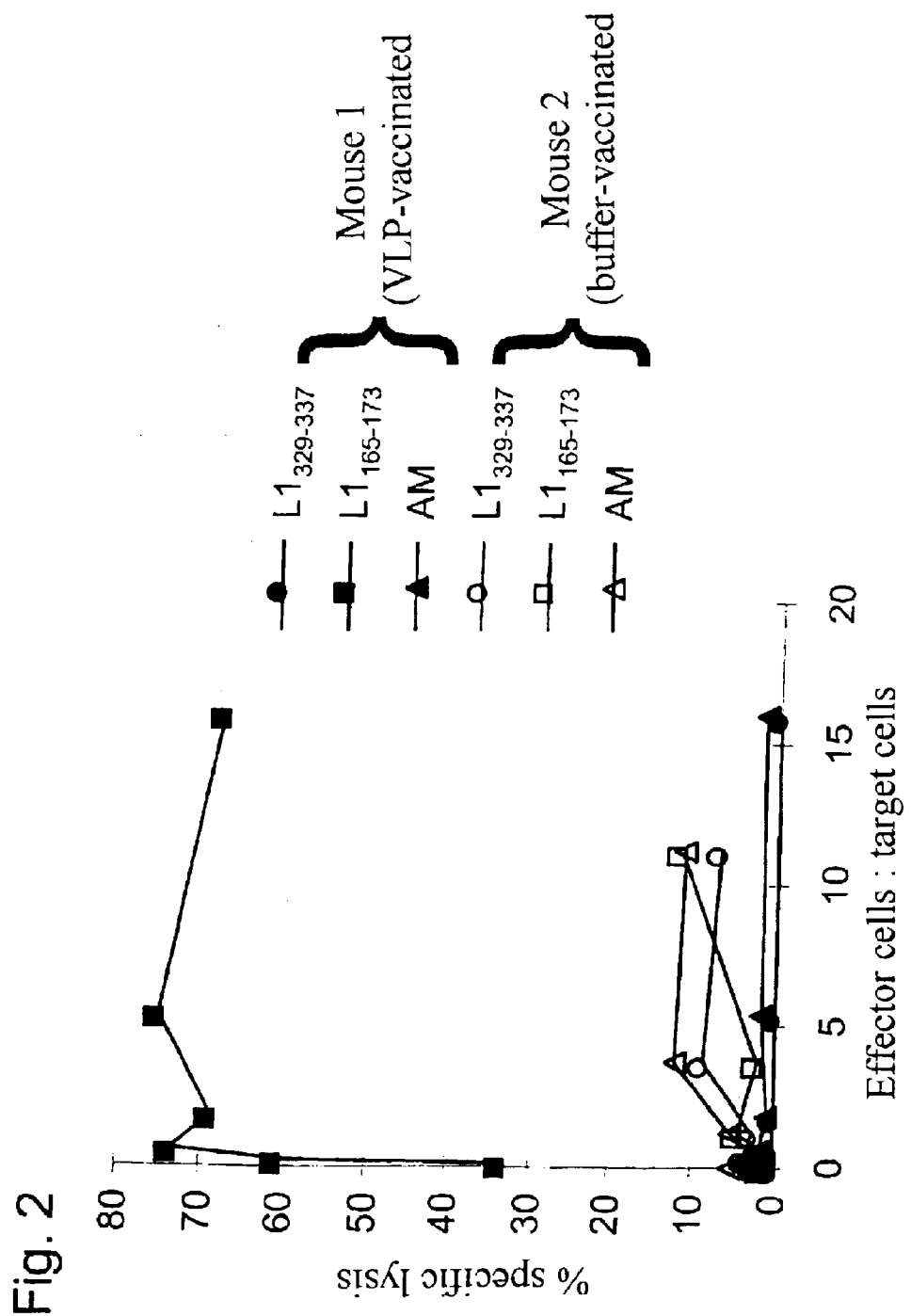
FIG. 2 shows the graphical analysis of the specific lysis of various RMA-S-cells which present either L1$_{330-338}$, L1$_{165-173}$ or AM by spleen cells of mice which had been vaccinated with VLPs or with buffer. The percentage of specific lysed cells is plotted as a function of the ratio of effector cells to target cells.

L1$_{330-338}$,

L1$_{165-173}$ or the AM peptide (as a control).

b) Cytotoxicity Assay of the Isolated Spleen Cells:

The stimulated spleen cells (effector cells) of mouse 1 (VLP-vaccinated) and 2 (buffer-vaccinated), prepared according to Example 1c, were incubated with the peptide-incubated RMA-S cells (target cells) in the presence of 0.5 μg/ml of the particular peptide in six different ratios of effector cells to target cells for 4 h. Specific lysis of the target cells was measured in a counter by the release of radioactive $^{51}$Cr (see FIG. 2).

Result: It was possible for the spleen cells of L1-immunized mouse 1 to effectively lyse the L1$_{165-173}$-preincubated target cells, whereas preincubation of RMA-S cells with L1$_{330-338}$ or the AM control peptide did not cause any distinct lysis of RMA-S cells by said stimulated spleen cells. The spleen cells of buffer-vaccinated mouse 2 showed no specific lytic activity for any of the peptide-preincubated RMA-S cells. Peptide L1$_{165-173}$ thus represents a specific cytotoxic T-cell epitope in said cells.

4. Peptide-Specific Lysis of Target Cells by L1-Specific T Cells (CVLP-Vaccinated Mouse)

a) Immunization of Mice With Cvlps:

A mouse was immunized with 10 μg of L1$_{Ac}$E7$_{1-55}$ CVLPs. Spleen cells were isolated after 2 weeks.

b) Preparation of Antigen-Presenting Cells:

EL4 cells were infected with MVA-L1$_{Ac}$, as described in 1b). RMA-S cells were loaded with L1$_{165-173}$, as described in 3a).

c) Restimulation of Isolated Spleen Cells:

The isolated spleen cells of 4a) were incubated with the two cell types EL4/MVA-L1$_{Ac}$ and RMA-S/L1$_{165-173}$ described under 4b) in each case for 12 days.

d) Cytotoxicity Assay of the Isolated Spleen Cells

Subsequently, a cytotoxicity assay was carried out in analogy to Example 2d) or 3b). In each case, lysis of EL4/MVA-L1$_{Ac}$ cells or RMA-S/L1$_{165-173}$ cells was determined in five different ratios of effector cells to target cells. The controls used were either EL4 cells which had been infected with an empty MVA-F6 vector, or RMA-S cells which had not been preincubated with L1$_{165-173}$ (see FIG. 3).

Figure 3:
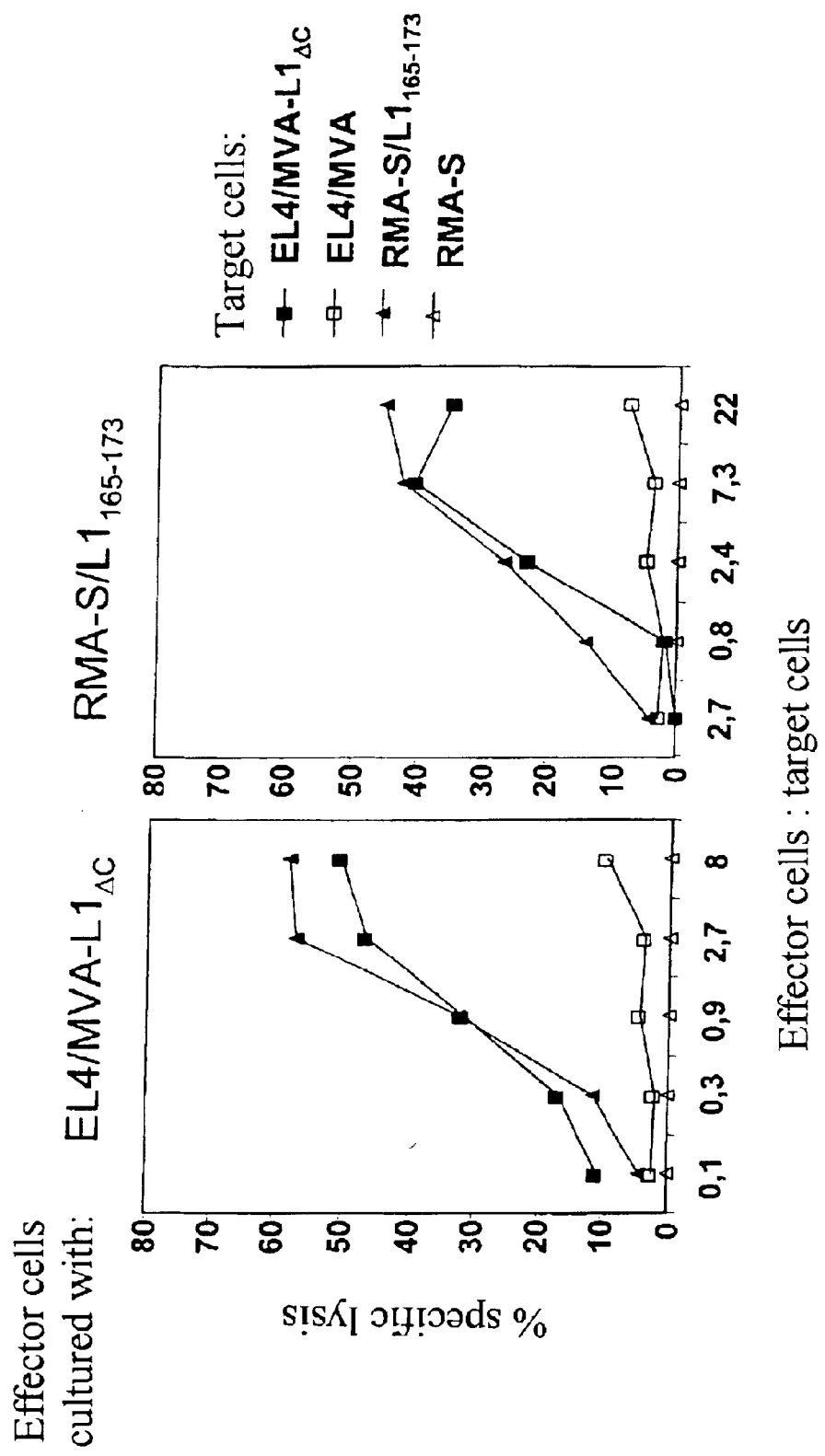
FIG. 3 shows the graphical analysis of the specific lysis of four different cell lines by T cells which had been restimulated beforehand with MVA-L1$_{AC}$-infected EL4 cells (left) or with RMA-S-cells loaded with L1$_{165-173}$. The percentage of specific lysed cells is plotted as a function of the ratio of effector cells to target cells.

Result: FIG. 3 shows the analysis of the $^{51}$Cr release assay in analogy to Example 1 or 2. The spleen cells, both after culturing together with EL4/MVA-L1$_{Ac}$ cells and after culturing together with RMA-S/L1$_{165-173}$ cells, were capable of effectively lysing the L1 peptide-presenting target cells (EL4/MVA-L1$_{Ac}$ cells or RMA-S/L1$_{165-173}$ cells), while the control cells were not lysed. Since recognition of L1-expressing cells is comparable to that of peptide-presenting cells, it can be concluded that peptide L1$_{165-173}$ is essentially responsible for inducing T-cell response.

This result again indicates that a CD8 T-cell response against HPV16 peptide L1$_{165-173}$ is induced in CVLP-vaccinated mice. In this connection, it is unimportant whether vaccination of the mice was carried out using VLPs (see Example 3) or CVLPs (this example).

5. L1-Specific Cytotoxic T Cells

Figure 4:
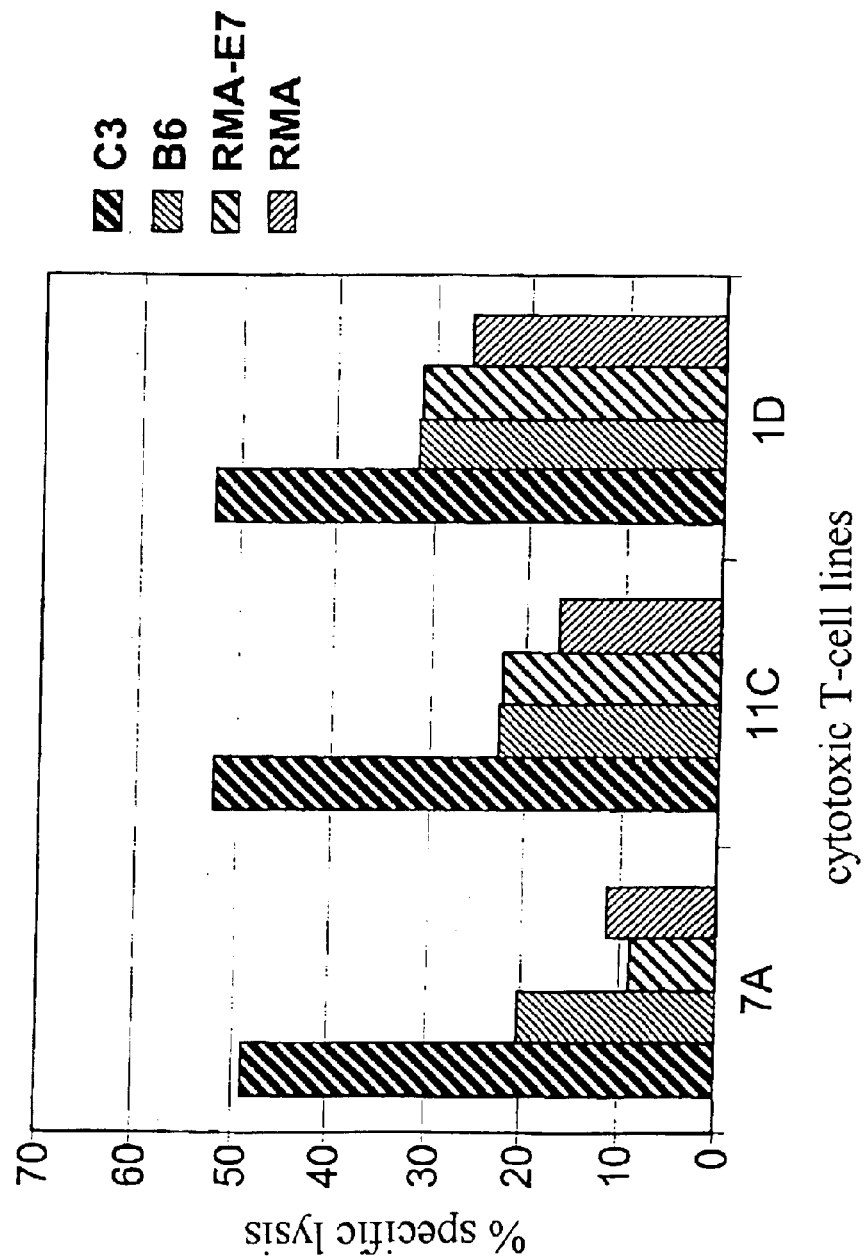
FIG. 4 shows the graphical analysis of the specific lysis of four different target cell lines by three different cytotoxic T-cell lines.

A mouse was vaccinated twice with 10$^7$ C3 cells (HPV16- and ras-transformed). The spleen cells were subsequently isolated and cultured in the presence of irradiated C3 cells as stimulator cells and restimulated by the addition of C3 cells. "Spleen cell clones" were cultured by thinning out the spleen cells. Said clones were then assayed in cytotoxicity assays on how efficiently they lyse C3 cells. In the same assay, said clones lysed substantially less efficiently B6, RMA or RMA-E7 cells (due to transformation with HPV16, C3 cells express E7, too). FIG. 4 shows three of these cytotoxic clones (=T-cell lines) which lyse C3 cells distinctly more efficiently than B6, RMA-E7 or RMA cells.

Figure 5:
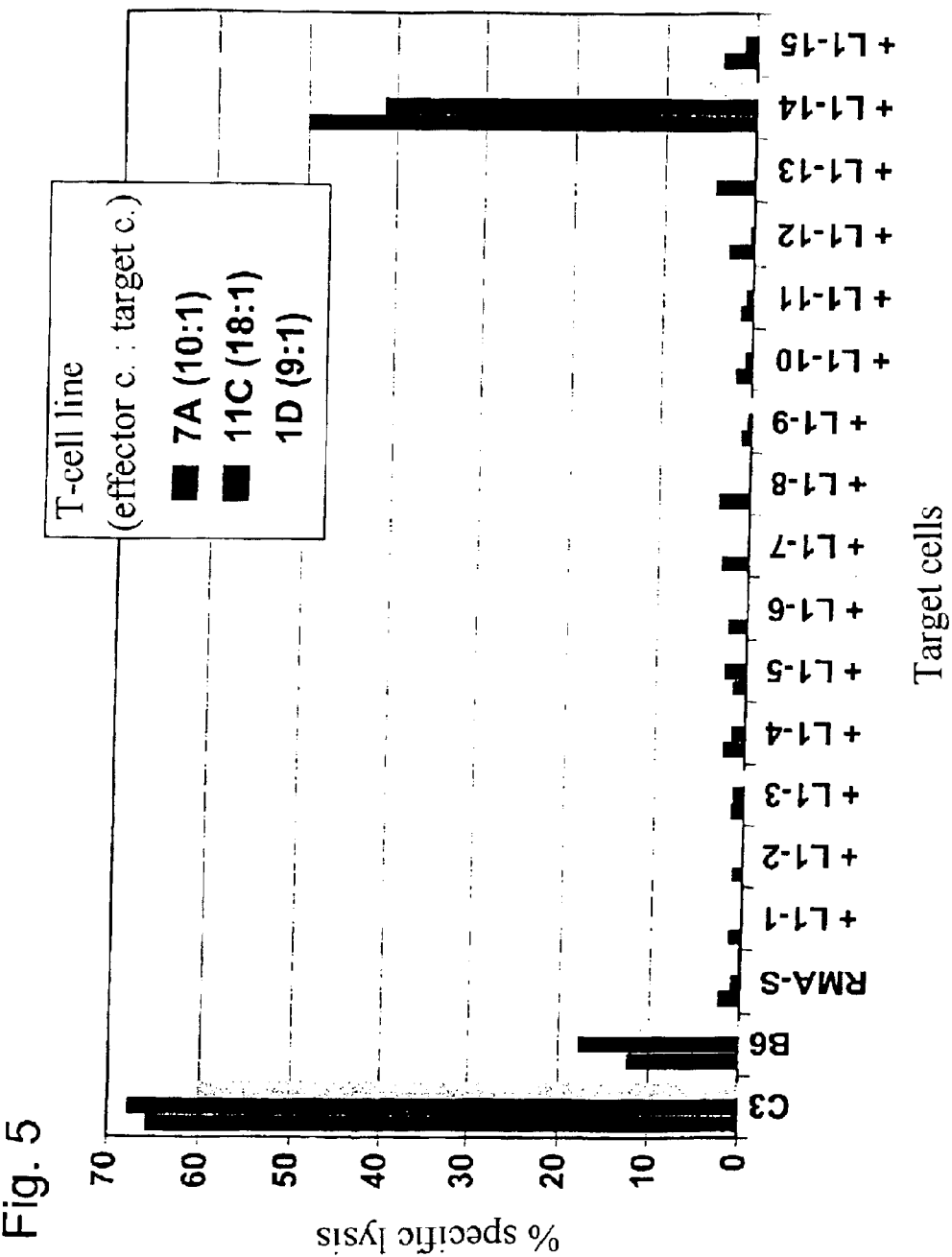
FIG. 5 shows the graphical analysis of the specific lysis of different target cells, either various cell lines or RMA-S-cells which had been loaded with L1 peptides L1-1 to L1-15, by three different cytotoxic T-cell lines.

Said three T-cell lines were then assayed in a cytotoxicity assay according to any of the preceding examples for their capability of lysing C3 cells, B6 cells, RMA-S cells and also RMA-S cells which had been loaded beforehand with various L1 peptides (L1-1 to L1-15; concentration in each case 50 μM). FIG. 5 shows that T-cell lines 7A and 11C are able to lyse very efficiently L1-14-loaded RMA-S cells. Thus, said T-cell lines are specific for peptide L1-14 which is L1 peptide 330–338 (L1$_{330-338}$). The other assayed peptides were not recognized by said T-cell lines. The sequences of said assayed peptides are as follows: L1-1: GAMDFTTL (SEQ ID NO: 4), L1-2: GDSLFFYL (SEQ ID NO: 5), L1-3: MQVTFIYI (SEQ ID NO: 6), L1-4: VYHIFFQM (SEQ ID NO: 7), L1-5: VHTGFGAM (SEQ ID NO: 8), L1-6: KYPDYIKM (SEQ ID NO: 9), L1-7: VTFIYILV (SEQ ID NO: 10), L1-8: LEDTYRFV (SEQ ID NO: 11), L1-9: GNQLFVTV (SEQ ID NO: 12), L1-10: KKYTFVTV (SEQ ID NO: 13), L1-11: ENDVNYHI (SEQ ID NO: 14), L1-12: AGVDNRECI (SEQ ID NO: 15), L1-13: TVGENVPDDL (SEQ ID NO: 16), L1-14: AQIFNKPYW (SEQ ID NO: 1), L1-15: YKNTNFKEYL (SEQ ID NO: 17)

What is claimed is:

1. A T-cell epitope consisting of an amino acid sequence selected from the group consisting of AQIFNKPYW (SEQ ID NO: 1) and AGVDNRECI (SEQ ID NO: 2).

* * * * *

UNITED STATES PATENT AND TRADEMARK OFFICE
CERTIFICATE OF CORRECTION

PATENT NO. : 6,911,207 B1  Page 1 of 1
APPLICATION NO. : 09/980064
DATED : June 28, 2005
INVENTOR(S) : Jochmus et al.

It is certified that error appears in the above-identified patent and that said Letters Patent is hereby corrected as shown below:

Column 5, Line 30ff., replace "Trichoplusia ni" with --*Trichoplusia ni*--.

Column 13, Line 41, replace "Cvlps" with --CVLPs--.

Signed and Sealed this

Twenty-third Day of January, 2007

JON W. DUDAS
*Director of the United States Patent and Trademark Office*